United States Patent [19]

Ruest et al.

[11] 4,059,579

[45] Nov. 22, 1977

[54] MORPHOLENONE DERIVATIVES

[75] Inventors: Dennis A. Ruest, Manchester; Roger L. Kidwell, Kirkwood; Chung Y. Shen, St. Louis, all of Mo.

[73] Assignee: Monsanto Company, St. Louis, Mo.

[21] Appl. No.: 513,792

[22] Filed: Oct. 10, 1974

[51] Int. Cl.² ........................................... C07D 295/00
[52] U.S. Cl. ............................ 544/172; 260/534 R; 260/518 R; 260/534 E; 560/170; 560/43; 560/44; 560/145
[58] Field of Search .................... 260/247.2 B, 244 R Primary Examiner—Paul J. Killos
Attorney, Agent, or Firm—E. P. Grattan; F. D. Shearin; N. E. Willis

[57] ABSTRACT

Novel imide carboxylates, O-carboxylates thereof, and amide carboxylates are useful as intermediates for preparation of sequestrant compounds.

3 Claims, No Drawings

MORPHOLENONE DERIVATIVES

BACKGROUND OF THE INVENTION

This invention relates to novel compounds useful as intermediates for making ether polycarboxylates and is a continuation-in-part of U.S. patent application Ser. No. 452,305, filed Mar. 18, 1974 now abandoned and copending herewith.

It is known that ether polycarboxylates represented by the formula

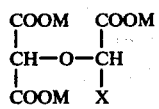

wherein M is alkali metal and X is hydrogen or COOM are useful as complexing agents for metal and alkaline earth metal ions and as detergency builders. Although methods for synthesis of such compounds (e.g., via Williamson ether type synthesis) have been disclosed, alternate processes for their preparation are desired. Accordingly, the provision of novel intermediates suitable for use in such alternate processes constitutes a significant contribution to the art.

SUMMARY OF THE INVENTION

This invention provides novel imide carboxylates, O-carboxylates thereof and amide carboxylates useful as intermediates for the preparation of the above described ether polycarboxylates and their acids and esters which are also intermediates for preparation of the salts. These compounds and their synthesis and use will be understood from the following description of the preferred embodiments.

DESCRIPTION OF THE PREFERRED EMBODIMENTS

The carboxylates of this invention are: imide carboxylates represented by the formula

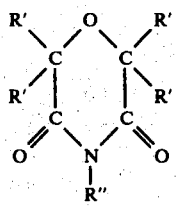

wherein the R' substituents are hydrogen, COOM', M' being alkali metal, ammonium or ½ magnesium (at least one R' substituent must be COOM') and the R" substituent is an alkyl group containing from 1 to 12 carbon atoms, phenyl, or COOM; acids and esters of such imide carboxylates; O-carboxylates of such imide carboxylates; amide carboxylates represented by the formula

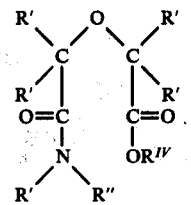

wherein $R^{IV}$ is an alkyl group containing 1 to 12 carbon atoms, hydrogen, M' or a phenyl group having 0 to 3 alkyl substituents containing 1 to 12 carbon atoms each and at least one of the R' substituents attached to a carbon atom is COOM'; and acids and esters of such amide carboxylates.

The carboxylates of this invention can be prepared by carboxylating one or both heterocyclic CH$_2$ moieties of imides represented by the formula

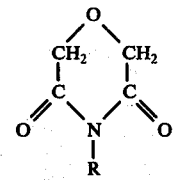

wherein R is hydrogen, an alkyl group containing from 1 to 12 carbon atoms or phenyl. (Such imides and methods for their preparation are known.) In some carboxylation procedures when R is hydrogen, the imide nitrogen may also be carboxylated. Generally, carboxylation of the imide will result in only monocarboxylation of one or both CH$_2$ moieties, however, under particularly severe carboxylation conditions, either or both CH$_2$ moieties may be dicarboxylated. Thus, the imide carboxylates formed can be represented by the formula

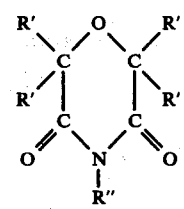

(I)

wherein R' is hydrogen or COOM' (M' being alkali metal, ammonium or ½ magnesium) and R" is an alkyl group containing 1 to 12 carbon atoms, phenyl, or COOM. At least one of the R' substituents must be COOM', it being understood that the R' substituents need not be identical. Depending on carboxylation conditions, acid or ester forms of such imide carboxylates, rather than the salt forms, can be obtained. Of course, the salt forms can also be converted to the acid or ester forms by conventional acidulation and esterification reactions. It will be recognized that certain imide carboxylates may exhibit enolate forms, e.g.

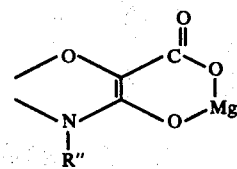

if M' is ½ Mg or

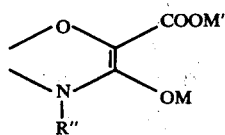

if M' is a monovalent metal. Although the imide carboxylates used in this invention are, for convenience, represented in both the specification and claims by the keto structure (I), this representation is intended to encompass the enolate forms of such compounds which may exist under various conditions.

Under carboxylation conditions, the imides and/or their carboxylates can form O-carboxylates (i.e., carbonates)

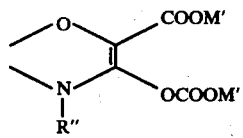

Such O-carboxylates are designated herein in the specification and claims as O-carboxylates of the imide carboxylates to clearly indicate their relationship to the imide carboxylates and to avoid the proliferation of nomenclature which would otherwise be required to designate configurations possible when one or both imide oxygens are carboxylated. It is to be understood, however, that no limitation that the O-carboxylates of the imide carboxylates must be derived from imide carboxylates is intended.

If the carboxylation reaction is conducted in the presence of alcohols, water, or a base, amide carboxylates

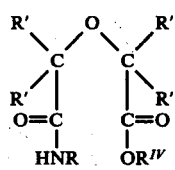

will be formed (such amide carboxylates can also be formed if the imide carboxylates are subsequently reacted with alcohol, water or a base) which upon further carboxylation will yield

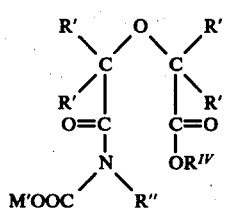

Thus, the above amide carboxylates can be collectively represented by the formula

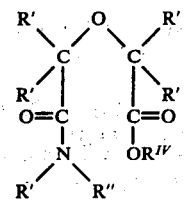

In the above three formulae, $R^{IV}$ is hydrogen, M', an alkyl group containing 1 to 12 carbon atoms, phenyl, or phenyl substituted with up to three alkyl groups containing 1 to 12 carbon atoms each and at least one of the R' substituents attached to a carbon atom is COOM'.

The desired $$\begin{array}{cc} COOM & COOM \\ | & | \\ CH-O-CH \\ | & | \\ COOM & X \end{array}$$

product or acids or esters thereof are obtained by hydrolyzing the imide or amide linkages of the above described imide carboxylates, O-carboxylates thereof and amide carboxylates. The term "hydrolyzing" is defined as encompassing hydrolysis reactions conducted in either acid or basic media or in the presence of alcohols in order to obtain the salt, acid or ester form as desired.

Hydrolysis, for example, by reaction of an alkali metal base (e.g., alkali metal hydroxide, carbonate, or bicarbonate) with carboxylates in which one —O-linked carbon atoms is carboxylated will yield

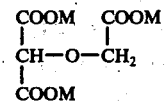

whereas reaction with carboxylates in which both —O-linked carbon atoms are carboxylated will yield

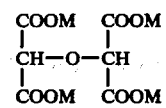

Dicarboxylated —O-linked carbon atoms, if formed, may lose one of the carboxylate substituents via decarboxylation in the hydrolysis reaction. The NR" moiety will be split out as an amine (or ammonia, if R" is COOM) in the reaction. The use of carboxylates wherein at least one R' substituent on each —O-linked carbon is hydrogen is preferred since such compounds are more easily formed than those containing dicarboxylated carbons.

The use of carboxylates in which only one —O-linked carbon is carboxylated is generally preferred since the ether tricarboxylate obtained by hydrolysis appears more readily biodegradable than the ether tetracarboxylates obtained from compounds in which both —O-linked carbons are carboxylated. However, in some applications mixtures of ether tri- and tetra-carboxylates provide superior builder performance, rendering the use of mixtures of compounds in which one and in which both —O-linked carbon atoms are carboxylated desirable.

Preferably, the above described imide carboxylates, O-carboxylates thereof and amide carboxylates of this invention are obtained by carboxylation of the imide as shown. All of the carboxylates described, including the acid and ester forms thereof, are considered as carboxylation products obtained by carboxylating at least one $CH_2$ moiety of the imide. It will be understood that the particular carboxylates or mixtures thereof obtained will be dependent on the carboxylation conditions and whether or not the water, alcohol or base required for amide carboxylate formation is present.

The carboxylation of the imide is preferably conducted in a solvent. Any solvent which does not participate unduly in competitive side reactions can be employed. In general, aprotic solvents having relatively high (1 or greater) dipole moments and dielectric constants greater than 10 or solvent mixtures containing at least 30% of such high dipole moment solvents are preferred since the use of solvents of higher dipole moments usually results in higher yields, particularly when alkali metal phenate - carbon dioxide complexes are employed as carboxylating agents as hereinafter described. For example, solvents such as dimethylformamide, hexamethyl phosphoric triamide, pyridine, dimethyl sulfoxide, tetramethylurea, N-methylpyrolidone, bis-2-methoxy ethyl ether, tetrahydrofuran and ethyl acetate can be employed for most carboxylation reactions. In some instances, the use of mixed solvent systems (including systems containing low dipole moment solvents such as benzene, toluene, hexane, etc., which, when used alone, do not generally provide good yields) improves yields and/or minimizes gel formation. Optimum solvents or solvent mixtures for particular reaction systems can be determined by routine testing.

If desired, the carboxylated imide can be separated from the reaction mixture by conventional means such as filtration, centrifugation, etc. In some instances, such as when alkali metal phenate $—CO_2$ complexes are employed as carboxylating agent, unreacted imide, phenol, and solvent may be somewhat difficult to separate from the carboxylated imide by mechanical means. In such cases, separation can be conveniently accomplished by adding water to form an aqueous phase containing the carboxylate and extracting the aqueous phase with a water immiscible solvent for the imide and phenol (but not the carboxylate) e.g., toluene or chloroform.

In one preferred method of making compounds of this invention, an imide, N-alkyl 3,5-morpholinedione is carboxylated by reaction with methyl methoxy magnesium carbonate. The carboxylation is preferably conducted in a solvent such as dimethyl formamide or a mixture of dimethyl formamide and bis-2-methoxy ethyl ether at temperatures of from 100° to 160° C., preferably 135° to 145° C. to provide reasonable reaction rates commensurate with minimum thermal decomposition. (This temperature range is convenient at atmospheric pressure. If pressures are reduced to facilitate methanol removal, the temperature range can be lowered.) This reaction, depending on concentration of reactants, length of reaction time, etc., can yield imide carboxylates in which one $CH_2$ moiety is carboxylated or in which both $CH_2$ moieties are carboxylated, or mixtures thereof. The ratio of compounds in which both $CH_2$ moieties are carboxylated can be increased by increasing the ratio of carboxylating agent to imide and/or prolonging the reaction. The ratio can, of course, be decreased by decreasing the amount of carboxylating agent and/or the reaction time.

The magnesium carboxylates thus obtained can be reacted with an alkali metal hydroxide to yield a mixture of ether tri- and tetra- carboxylates. Preferably, however, the magnesium carboxylates are first dissolved in cold phosphoric acid and treated with ammonia to precipitate magnesium and form the ammonium carboxylates which are then reacted with the alkali metal hydroxide.

In another preferred embodiment of making compounds of the invention, the imide is carboxylated by reaction with a carboxylating agent formed by combining carbon dioxide with a phenate represented by the formula

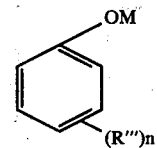

wherein $R'''$ is an alkyl group containing from 1 to 12 carbon atoms and $n$ is an integer from 0 to 3. (Carboxylating agents of this type are described in U.S. Pat. No. 3,658,874, the disclosure of said patent being incorporated herein by reference.) The carboxylation is preferably conducted in a high dipole moment solvent as previously discussed at temperatures of from 0° to 150° C., preferably 25° C. to 100° C. under sufficient pressure to prevent loss of carbon dioxide. Solvent, temperature, and pressure will, of course, be correlated to optimize solubility, reaction rate, etc. The reaction can provide imide carboxylates in which one or both $CH_2$ moieties are carboxylated, or mixtures thereof. The relative amounts of these compounds can be varied by adjustment of the amount of carboxylating agent and reaction time as in the previously described embodiment of this invention. This embodiment also generally leads to the formation of O-carboxylates, e.g.

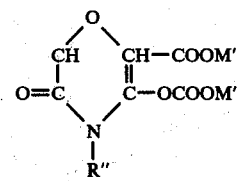

amides, e.g.

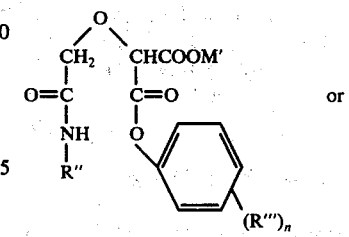

or

-continued

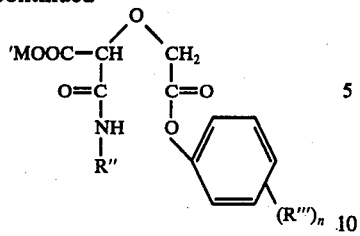

and amide carboxylates, e.g.

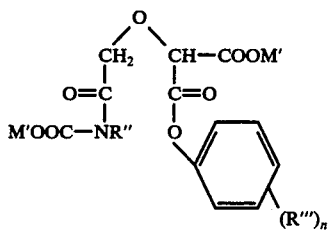

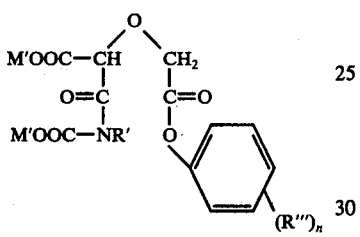

as well as imide carboxylates.

Carboxylation of the imide can also be accomplished in multiple step reactions. For example, the imide

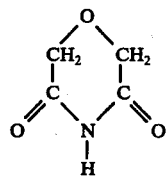

can be reacted with lithium diisopropyl amide (preferably in tetrahydrofuran at about −40° C. to −70° C.) and the reaction product treated with carbon dioxide to carboxylate (COOLi substituents) one $CH_2$ moiety and the imide nitrogen.

Carboxylation of imides can also be accomplished by using an alkali metal carbonate salt under $CO_2$ pressure, preferably at a temperature between 140° C. - 270° C. Conversion rate generally increases as $CO_2$ pressure increases. The $CO_2$ pressure required to obtain a particular conversion rate can be reduced by use of catalysts such as group VIII transition metals and their derivatives, for example, iron and nickel, and group IB and VB metals and their derivatives. The use solvents such as of molten low melting salts, e.g. sodium formate as solvents can accelerate the reaction, improve heat transfer, and facilitate removal of reaction products.

Other suitable carboxylating agents and optimum conditions for their use can be determined by routine testing.

Preferably, the carboxylates (I, II, III) are reacted with alkali metal base (usually at least 2% stoichiometric excess base and temperatures of 90° C. to 150° C. are employed) to yield

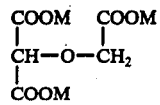

and/or

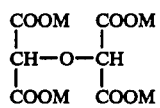

Alternately, these products can be obtained by acid hydrolysis of such carboxylates (preferably with aqueous mineral acid at temperatures of 25° to 100° C.) and neutralization of the hydrolysis product with alkali metal base. Generally, the direct reaction of the carboxylate with alkali metal base is preferred to avoid possible decarboxylation during hydrolysis and/or salt formation. The use of sodium or potassium hydroxide, particularly sodium hydroxide in the saponification or neutralization reaction is preferred in view of the preference for the corresponding sodium or potassium ether carboxylates as detergency builders.

The preparation of compounds of this invention and their utility is further illustrated by the following examples wherein all parts and percentages are by weight unless otherwise indicated.

EXAMPLE I

About 14 grams sodium phenoxide in 100 ml. dimethylformamide is stirred under a carbon dioxide atmosphere, the temperature being allowed to rise from 25° C. to 33° C. over a period of 5 to 10 minutes. Formation of a precipitate which dissolves on further stirring as the mixture is allowed to cool to 25° C. is observed. After about 3 hours, the carbon dioxide atmosphere is replaced with nitrogen atmosphere and a solution of about 7.7 grams N-methyl 3,5-morpholinedione in 20 ml. of dimethylformamide is added to the mixture which is then allowed to stand for about 20 hours. The reaction mixture is poured into 200 ml. diethyl ether and filtered to isolate the imide carboxylate as a white solid which is dissolved in 100 ml. water. Sodium hydroxide (20 grams) is added and the solution is maintained at 85° C. for 2 hours with stirring. The solution is concentrated to about 50 ml. by vacuum distillation.

Addition of 200 ml. methanol precipitates a solid product identified by nuclear magnetic resonance analysis as

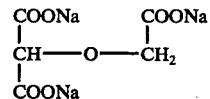

Repeating the above procedure using a 4:1 mole ratio of carboxylating agent to imide yields a mixture of

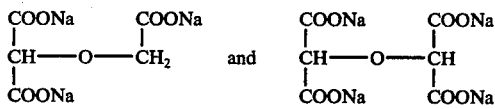

EXAMPLE II

About 115 ml. 2.3 molar hexane solution of n-butyllithium is added, under nitrogen atmosphere, to a mixture of 400 ml. tetrahydrofuran and 24 grams diisopropyl amine precooled to −40° C. The mixture is cooled to −70° C. and a solution of 12.5 grams 3,5-morpholinedione in 100 ml. tetrahydrofuran is added and a stream of carbon dioxide is bubbled into the mixture for about one hour. The mixture is evaporated, leaving a dry powder residue containing

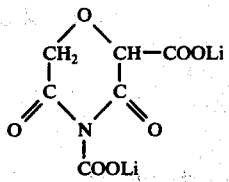

which is dissolved in 150 ml. water and passed through an acid ion exchange column (packed with a sulfonated polystyrene resin marketed by Fisher Scientific Company under the trademark REXYN 101). The acid solution is neutralized with sodium hydroxide. Nuclear magnetic resonance analysis shows the solution to contain sodium 3,5-morpholinedione-2-carboxylate. Reaction of this product with hot sodium hydroxide and addition of methanol as in Example I yields

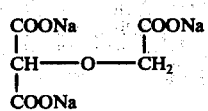

EXAMPLE III

Carbon dioxide is bubbled through a mixture of about 16 grams of potassium phenoxide in 100 ml. dimethylformamide. The temperature rises from 25° C. to 41° C. in about 10 minutes and slowly drops back to 25° C., the formation and dissolution of a solid being observed. After 3 hours carbon dioxide bubbling is stopped and the mixture is placed under nitrogen atmosphere, a solution of 7.7 grams N-methyl 3,5-morpholinedione in 15 ml. dimethylformamide is added and the mixture allowed to stand 4 days at about 25° C. The mixture is then poured into 200 ml. diethyl ether and filtered to recover a solid which is dissolved in 100 ml. water and reacted with 20 grams sodium hydroxide at 85° C. for 2 hours to yield

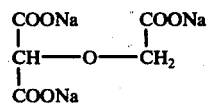

in admixture with some potassium salts.

EXAMPLE IV

About 0.05 mole N-methyl 3,5-morpholinedione in 12 ml. dimethylformamide is added over a period of about 40 minutes to 1.4 mole methyl methoxy magnesium carbonate in 50 ml. of a 75%/25% mixture bis-2-methoxy ethyl ether/dimethylformamide and the resulting mixture is maintained in the temperature range of 120° to 140° C. for 1 hour. The mixture is poured into 200 ml. ethyl ether and filtered to recover solid magnesium imide carboxylate product which is added to aqueous phosphoric acid (containing 1 mole $H_3PO_4$ per mole of magnesium in the original methyl methoxy magnesium carbonate solution) and the resulting solution is neutralized to a pH of 9 with ammonia, forming ammonium salt of the carboxylate and precipitating the magnesium as hydrated $MgNH_4PO_4$. The carboxylate solution is separated from the precipitate by filtration and reacted with excess sodium hydroxide for 2 hours at 85° C. to yield

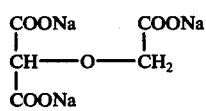

EXAMPLE V

About 12.9 grams N-methyl 3,5-morpholinedione and 41.5 grams potassium carbonate are heated to 200° C. under $CO_2$ pressure of 200 atmospheres for about 2½ hours. The product is cooled, dissolved in water. Potassium hydroxide is added and the mixture boiled to remove methyl amine and evaporated to dryness. Analysis shows the product to contain

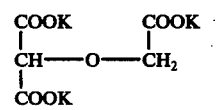

EXAMPLE VI

Two mixtures containing 1 mole N-methyl 3,5-morpholinedione and 3 moles sodium carbonate are prepared. One mixture is heated to and maintained at about 215° C. under 150 atmospheres carbon dioxide pressure for 2 hours. The other mixture is treated in the same manner after being admixed with 2 moles sodium formate.

Both mixtures are then cooled, dissolved in water, reacted with sodium hydroxide and heated to expel methyl amine.

Analysis shows both mixtures to contain

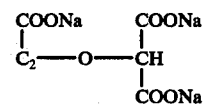

with about five-fold greater yield being obtained from the sodium formate containing mixture. It is believed that the sodium formate promotes the reaction by functioning as a solvent for the N-methyl 3,5-morpholinedione sodium carbonate mixture.

EXAMPLE VII

About 0.05 mole N-methyl 3,5-morpholinedione in 12 ml. dimethylformamide is added over a period of about 40 minutes to 1.4 mole methyl methoxy magnesium carbonate in 50 ml. of a 75%/25% mixture bis-2-methoxy ethyl ether/dimethylformamide and the resulting mixture is maintained in the temperature range of 120° to 140° C. for 1 hour. The mixture is poured into 200 ml. ethyl ether and filtered to recover solid magnesium imide carboxylate product which is added to aqueous phosphoric acid (containing 1 mole $H_3PO_4$ per mole to magnesium in the original methyl methoxy magnesium carbonate solution) and the resulting solution is neutralized to a pH of 9 with ammonia, forming ammonium salt of the carboxylate and precipitating the magnesium as hydrated MgNH$_4$PO$_4$.

The carboxylate solution is separated from the precipitate by filtration and is concentrated to a syrup-like consistency. Ethyl alcohol is added and crystals of

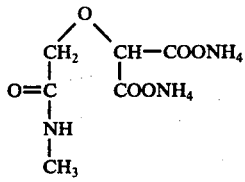

precipitate. This product is boiled in sodium hydroxide solution to expel ammonia and amine and yield

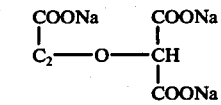

EXAMPLES VIII – X

The procedure of Example I is repeated with the imides shown in the following table being substituted for N-methyl 3,5-morpholinedione:

| EXAMPLE | IMIDE |
|---|---|
| VIII | 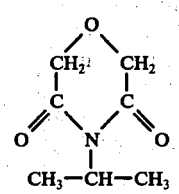 |
| IX | (structure shown) |
| X | (structure shown with C$_{12}$H$_{25}$ and phenyl) |

In each example, the product

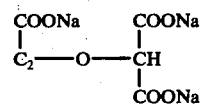

is obtained.

EXAMPLE XI

The procedure of Example I is repeated using various solvents shown in the following table and a 2:1 mole ratio of carboxylating agent to imide. Product yields are shown based on imide charged to the reactions.

| Solvent | Dipole Moment | Donicity | % yield CH$_2$ O CH COONa (COONa, COONa) | % yield CH O CH COONa (COONa, COONa) |
|---|---|---|---|---|
| dimethyl formamide | 3.86 | 26.6 | 48 | <1 |
| hexamethyl phosphotriamide | 4.31 | 38.8 | 68 | 2 |
| ethyl acetate | 1.88 | 17.1 | 16 | <1 |
| bis-2-methoxy ethyl ether | 1.97 | not determined | 22 | 3 |
| nitrobenzene | 4.03 | 4.4 | 1 | <1 |
| tetramethyl urea | 3.47 | 29.6 | 44 | 2 |
| hexane | 0.085 | not determined | 1 | <1 |
| acetonitrile | 3.44 | 14.1 | 24 | <1 |
| dimethylsulfoxide | 3.9 | 29.8 | 49 | <1 |
| tetrahydrofuran | 1.75 | 20.0 | 23 | 1 |
| N-methylpyrolidone | 4.09 | not determined | 46 | 1 |
| benzene | 0 | 4.9 (calculated) | <1 | <1 |
| pyridine | 2.37 | 33.1 | 40 | 1 |
| toluene | 0.31 | not determined | 2 | <1 |

It is seen from the above data that high dipole moment and donicity (a measure of basicity) generally are correlated with higher yields.

EXAMPLE XII

Anhydrous sodium phenate (232 gms) is dispersed in a mixed solvent consisting of 350 ml. toluene and 350 ml. dimethylformamide. Carbon dioxide is sparged into the mixture for about 30 minutes, temperature of the mixture being maintained at 25° C. Crystalline N- methyl 3,5-morpholinedione (128 gms) is added and the mixture is maintained at 45° C. under about 1.7 atmospheres carbon dioxide pressure. About 800 ml. water is added to the reaction mixture containing carboxylate product, predominantly

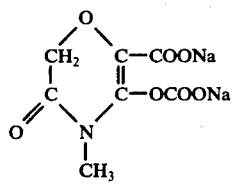

a major portion of which is converted to

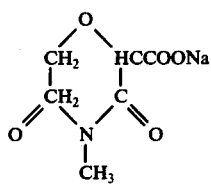

by hydrolysis.

An aqueous phase containing the carboxylates and sodium bicarbonate is separated. The aqueous phase is extracted with chloroform to remove residual solvent. Sodium hydroxide is added to the aqueous phase which is then boiled to convert the imide carboxylates and hydrolysis products thereof to trisodium 2 oxa-1,1,3-propane tricarboxylate.

The organic phase and chloroform extract are combined and distilled to recover unreacted N-methyl 3,5-morpholinedione which is recycled.

EXAMPLE XIII

One liter of a 2 molar solution of sodium phenate in pyridine is prepared by distilling a mixture of phenol, 50% aqueous sodium hydroxide and pyridine to remove water. The solution is cooled to 50° C. and sparged with carbon dioxide for about 30 minutes. One gram mole of N-methyl 3,5-morpholinedione is added and the reaction mixture is maintained at 50° C. for 4 hours. About 800 ml. of water is added and the mixture is counter currently extracted with 800 ml. toluene in three stages to remove phenol, unreacted N-methyl 3,5-morpholinedione and pyridine. The remaining aqueous phase is boiled to drive off any remaining solvent and consume carbonate by the reactions

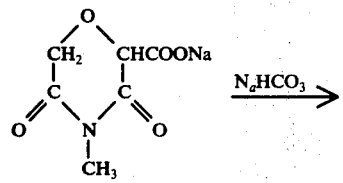

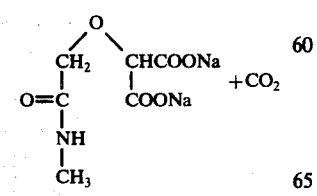

and

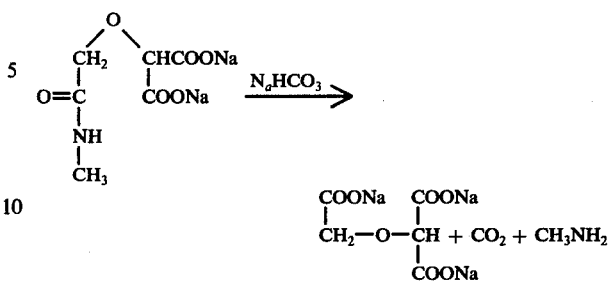

Sodium hydroxide is added to convert remaining imide carboxylate and amide carboxylate to

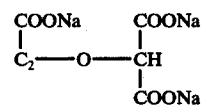

The organic phase is distilled to recover raw materials and solvents which are recycled.

What is claimed is:

1. A compound represented by the formula:

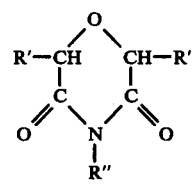

wherein R' is selected from the group consisting of hydrogen and COOM', M' being alkali metal, ammonium or one-half magnesium, hydrogen, or alkyl radicals containing 1 to 12 carbon atoms, provided that at least one R' substituent is COOM' and R" is selected from the group consisting of alkyl radicals containing from 1 to 12 carbon atoms, phenyl and COOM, M being alkali metal; and, the O-carboxylates of the said imide carboxylates.

2. A compound according to claim 1 represented by the formula:

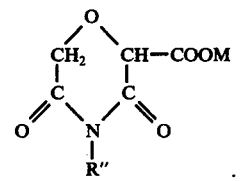

3. A compound according to claim 2 represented by the formula:

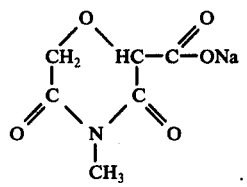

* * * * *

UNITED STATES PATENT OFFICE
CERTIFICATE OF CORRECTION

PATENT NO. : 4,059,579
DATED : November 22, 1977
INVENTOR(S) : Dennis A. Ruest et al It is certified that error appears in the above-identified patent and that said Letters Patent are hereby corrected as shown below:

Column 10, line 45; Column 11, line 20; Column 12, line 20; and Column 14, line 20

"$\begin{array}{cc} COONa & COONa \\ | & | \\ C_2 - O - CH & \\ & | \\ & COONa \end{array}$"   should be --- $\begin{array}{cc} COONa & COONa \\ | & | \\ CH_2 - O - CH & \\ & | \\ & COONa \end{array}$ ---.

Signed and Sealed this

Twenty-first Day of March 1978

[SEAL]

Attest:

RUTH C. MASON
Attesting Officer

LUTRELLE F. PARKER
Acting Commissioner of Patents and Trademarks